(12) United States Patent
Richards

(10) Patent No.: US 10,363,381 B2
(45) Date of Patent: Jul. 30, 2019

(54) MEDICAL INFUSION FLUID HEAT EXCHANGE APPARATUS AND WARMING SYSTEMS

(71) Applicant: SMITHS MEDICAL INTERNATIONAL LIMITED, Kent (GB)

(72) Inventor: Fredrick M Richards, Plymouth, MA (US)

(73) Assignee: Smiths Medical International Limited, Kent (GB)

( * ) Notice: Subject to any disclaimer, the term of this patent is extended or adjusted under 35 U.S.C. 154(b) by 445 days.

(21) Appl. No.: 14/762,345

(22) PCT Filed: Dec. 13, 2013

(86) PCT No.: PCT/GB2013/000548
§ 371 (c)(1),
(2) Date: Jul. 21, 2015

(87) PCT Pub. No.: WO2014/118487
PCT Pub. Date: Aug. 7, 2014

(65) Prior Publication Data
US 2015/0359976 A1 Dec. 17, 2015

(30) Foreign Application Priority Data
Jan. 31, 2013 (GB) .................................. 1301736.3

(51) Int. Cl.
*A61M 5/44* (2006.01)
*F28D 7/10* (2006.01)
*F28D 21/00* (2006.01)

(52) U.S. Cl.
CPC ............... *A61M 5/44* (2013.01); *F28D 7/106* (2013.01); *A61M 2205/36* (2013.01); *A61M 2205/366* (2013.01); *F28D 2021/005* (2013.01)

(58) Field of Classification Search
CPC ............ A61M 5/44; A61M 2205/3653; A61M 2205/366; A61M 2205/3633;
(Continued)

(56) References Cited

U.S. PATENT DOCUMENTS

| 4,306,018 A | 12/1981 | Kirkpatrick |
| 4,678,460 A | 7/1987 | Rosner |

(Continued)

FOREIGN PATENT DOCUMENTS

| JP | 57079536 | 5/1982 |
| WO | WO 01/56638 A1 | 8/2001 |
| WO | WO 02/15967 A1 | 2/2002 |

OTHER PUBLICATIONS

PCT International Search Report and Written Opinion of the ISA/EP, PCT/GB2013/000548, dated May 3, 2014.

*Primary Examiner* — Emily L Schmidt
(74) *Attorney, Agent, or Firm* — Louis Woo

(57) ABSTRACT

Apparatus for warming medical infusion fluids includes a heat pipe (12) warmed by an electrical heater (17) at one end. A replaceable fluid flow path (20) of helical configuration extends along the heat pipe (12) and is formed between an inner, thermally-conductive sleeve (21) with a helical profile and an outer insulative sleeve (26). An inlet (3) to the flow path (20) is located adjacent the heater (17), the outlet (4) being at the opposite end of the heat pipe (12). The inlet (3) is connected to a suspended saline bag (1) and the outlet (4) connects via tubing (5) to a catheter (6) inserted in a blood vessel. A temperature sensor (18) in the outlet tubing (5) provides a feedback output to a control unit (11) that controls operation of the heater (17) to maintain a stable temperature.

7 Claims, 2 Drawing Sheets

(58) Field of Classification Search
CPC ............ A61M 2205/3673; F28D 7/106; F28D 2021/005; F28F 21/04; F28F 1/105; F28F 1/20
See application file for complete search history.

(56) References Cited

U.S. PATENT DOCUMENTS

| | | |
|---|---|---|
| 4,878,537 A | 11/1989 | Verkaart |
| 5,063,994 A | 11/1991 | Verkaart |
| 5,097,898 A | 3/1992 | Verkaart |
| 5,290,237 A | 3/1994 | Verkaart |
| 5,417,274 A | 5/1995 | Verkaart |
| 5,707,431 A | 1/1998 | Verkaart |
| 5,713,864 A | 2/1998 | Verkaart |
| 5,807,332 A | 9/1998 | Augustine |
| 6,074,363 A | 6/2000 | Beran |
| 6,139,528 A | 10/2000 | Kistner et al. |
| 6,257,265 B1 | 7/2001 | Brunner |
| 6,259,074 B1 | 7/2001 | Brunner |
| 6,641,556 B1 | 11/2003 | Shigezawa |
| 7,867,188 B2 | 1/2011 | Frey |
| 2002/0151945 A1* | 10/2002 | Gobin ............... A61F 7/12 607/105 |
| 2008/0077087 A1 | 3/2008 | Martens |
| 2009/0159248 A1* | 6/2009 | Mimitz, Sr. ........ B21C 37/207 165/154 |
| 2012/0325826 A1* | 12/2012 | McCormick .......... A61M 5/44 220/592.01 |

* cited by examiner

MEDICAL INFUSION FLUID HEAT EXCHANGE APPARATUS AND WARMING SYSTEMS

This invention relates to medical infusion fluid heat exchange apparatus and warming systems.

The invention is more particularly concerned with heat exchange apparatus and warming systems for use in medical applications for heating fluid supplied to the body.

It is common practice to warm fluids, such as blood and infusion fluids, supplied to the body. Ideally the fluid supplied to the body should be as close as possible to normal body temperature. One way of doing this is to pass the infusion fluid through a heat exchanger that is connected with a circulating supply of warmed water so that the heat in the water is transferred to the infusion fluid. Apparatus for warming fluid in this way is available from Smiths Medical under the Hotline® trade mark (Hotline is a Registered Trade Mark of Smiths Medical ASD, Inc). Fluid warmers can alternatively include an electrical resistance heater in thermal contact with the infusion fluid. Examples of medical fluid warmers are described in: U.S. Pat. Nos. 5,063,994, 5,097,898, 5,290,237, 5,707,431, 7,867,188, 5,417,274, 4,878,537, 5,713,864, 4,678,460, 6,257,265, 6,259,074, 6,074,363 and 6,641,556. Ideally such fluid warmers should provide a very stable warming effect over a range of flow rates. The warmer should be compact and give an efficient transfer of heat to the infusion fluid with a low rate of loss to the surroundings. The warmer should present a low risk of infection and have effective electrical isolation to minimise risk to the patient. The warmer, especially any disposable components of the warmer, should be capable of manufacture at low cost.

It is an object of the present invention to provide alternative heat exchange apparatus and warming systems.

According to one aspect of the present invention there is provided apparatus of the above-specified kind, characterised in that the apparatus includes an elongate heat pipe, a heat source mounted in thermal contact with one end of the heat pipe and an infusion fluid flow path extending along the outside of the heat pipe in thermal contact with the heat pipe, and that the heat source transfers heat to the heat pipe and the heat pipe transfers heat to the fluid flowing along the flow path.

The fluid flow path along the heat pipe preferably has a length exceeding the length of the heat pipe and may extend helically along and around the outside of the heat pipe. The fluid flow path may be provided between an inner sleeve of a thermally-conductive material having a helical external profile and an outer sleeve extending coaxially around the inner sleeve. A heat transfer substance may fill space between the outside of the heat pipe and the inner surface of the inner sleeve. The outer sleeve is preferably of a thermally-insulative material. The fluid flow path is preferably separable from the heat pipe so that it can be removed and replaced for use on different patients. Alternatively, the heat pipe may have an external surface with a helical profile, the flow path being defined between the external surface of the heat pipe and an outer sleeve. The heat source may include a positive temperature coefficient heater. The inlet of the infusion flow path is preferably adjacent the heat source at one end of the heat pipe, the outlet of the infusion flow path being located towards the opposite end of the heat pipe. The apparatus preferably includes a control unit arranged to control the heat source and a temperature sensor located in an outlet path of the apparatus, the output of the temperature sensor being supplied to the control unit. The control unit is preferably arranged to control the temperature of the fluid at the outlet to be substantially 37° C.

According to another aspect of the present invention there is provided a medical infusion fluid warming system including heat exchange apparatus according to the above one aspect of the present invention, characterised in that the system includes a source of infusion fluid connected with an inlet of the infusion flow path, and a fluid connection extending between an outlet of the infusion flow path and a catheter connected with a patient such that fluid from the fluid source is warmed by the heat exchange apparatus and supplied to the patient via the catheter.

The source of infusion fluid may be a suspended bag of saline. The inlet of the infusion flow path is preferably located towards the end of the heat pipe at which the heat source is mounted.

A medical infusion fluid warming system including a heat exchanger in accordance with the present invention, will now be described, by way of example, with reference to the accompanying drawings, in which.

Figure 1:
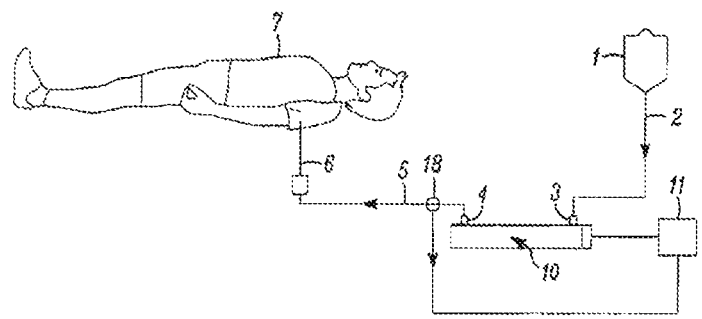
FIG. 1 shows the system schematically.

With reference first to FIG. 1, the fluid warming system includes a source of infusion fluid, such as a suspended bag 1 of saline, although other sources such as a rapid infusor, an infusion pump or the like could be used. The bag 1 is connected via tubing 2 to the inlet 3 of the heat exchanger 10. A conventional flow regulator (not shown) could be included in the tubing 2 at some point along its length. The heat exchanger 10 is controlled by a power supply and control unit 11 and warms the fluid supplied to it, which flows out via an outlet 4 to one end of outlet tubing 5. The other end of the outlet tubing 5 is connected to a catheter 6, such as an intravenous catheter, which is connected with patient 7, such as by having its patient end inserted in a blood vessel.

Figure 2:
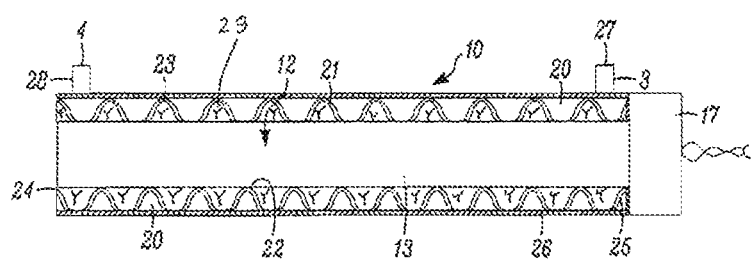
FIG. 2 is a cross-sectional side elevation view of the heat exchanger.
Figure 3:
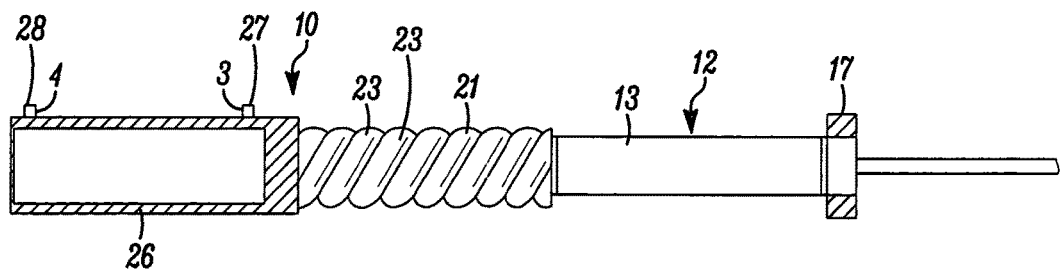
FIG. 3 is a side elevation view of the heat exchanger with its different components separated.
Figure 4:
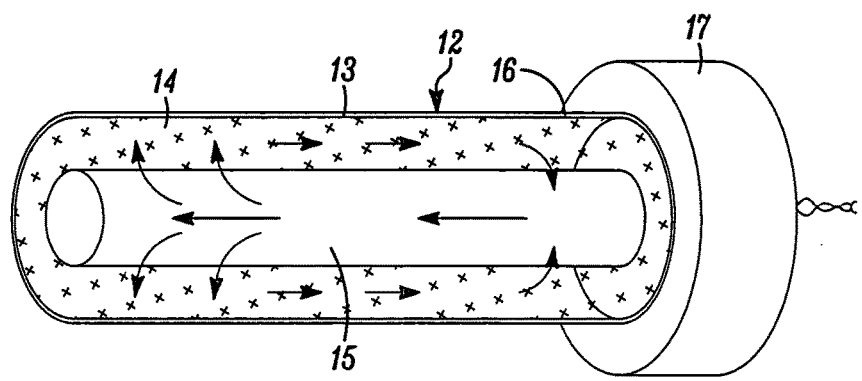
FIG. 4 is a perspective view showing the operation of the heat pipe.

As so far described, the system is conventional but differs from previous systems in the nature of the heat exchanger 10, which is shown in more detail in FIGS. 2 to 4.

The heat exchanger 10 employs a heat pipe 12 to warm the infusion fluid. The heat pipe 12 is typically of cylindrical shape being about 12 mm to 25 mm in external diameter. The length of the heat pipe 12 depends on the amount of heating needed, which in turn is dependent on the expected fluid flow rate and initial temperature. The heat pipe 12 has a sealed outer wall or casing 13 of a thermally-conductive material, such as aluminum or another metal. The casing 13 is evacuated of air and contains a small amount of a working fluid such as of ethanol, ammonia, acetone, water or the like. A capillary or wicking sleeve 14 extends along the inside of the casing 13 and defines a central, coaxial vapour cavity 15 extending along the length of the heat pipe. When the right-hand end 16 of the heat pipe 12 is heated it causes a phase change by evaporating the working fluid at that end from a liquid to a vapour, which takes up the latent heat of vaporisation. The vapour flows to the left along the cavity 15 to the opposite end of the casing 13 and, as it does so, it cools and condenses back to a liquid, thereby producing another phase change and giving up its stored thermal energy to the opposite end of the heat pipe 12. The condensed vapour, now in liquid form, is absorbed by the surrounding wicking sleeve 14 where it is drawn back to the right through the wicking material to the heated end of the heat pipe 12 to repeat the cycle. The term "heat pipe" is intended to include any heat transfer device that operates using phase transition between a vapour and a liquid.

The heat pipe 12 is attached at its right-hand end in thermal contact with a heat source provided by a temperature-controlled electrical heater, such as a positive temperature coefficient heater 17. The heater 17 is connected to the power supply and control unit 11 to provide the appropriate level of heating according to the fluid supplied to the heat exchanger 10. The system preferably includes a temperature sensor 18 connected somewhere in the flow path from the outlet 4 to provide a feedback signal to the control unit 11 and may also include a temperature sensor connected at the inlet 3 to monitor the temperature of the fluid supplied to the heat exchanger 10. In this way, the heater 17 can be controlled to ensure that fluid is supplied at the outlet 4 at the desired temperature.

Fluid supplied to the heat exchanger 10 flows along the outside of the heat pipe 12, entering at the heater end of the pipe and emerging at the opposite end after having followed a flow path the length of which is greater than the length of the heat pipe. More particularly, the heat exchanger has a helical flow path 20 along and around the heat pipe 12. This helical flow path 20 can be formed in various different ways but, in the present example, is achieved by an inner sleeve 21 of a thermally-conductive material such as a metal (for example, aluminum), a plastics or a ceramic, or some combination of these materials. As well as being thermally-conductive, the material must be biocompatible with the fluid being heated, or it could be coated with a layer of biocompatible material. The inner surface 22 of the sleeve 21 is in close thermal contact with the outside of the heat pipe 12 and is slidable along it. Externally, the sleeve 21 is formed with a single-start helical flute or ridge 23 and provides the inner surface of the flow path 20 for the fluid. The inner surface 22 of the sleeve 21 could be flat to lie in contact with the heat pipe 12 in order to maximise heat transfer between the heat pipe and the sleeve. Alternatively, the inner surface 22 of the sleeve 21 could have the same profile as its outer surface, which would mean that the sleeve would only contact the heat pipe 12 along the locus of the peak of the ridge 23. If such a sleeve 21 were used it would be desirable to fill the valley space between the sleeve and the outside of the heat pipe 12 with a heat transfer substance 29 (shown as Ys) such as a paste or gel to promote heat transfer across the valley. Instead of providing the inner surface of the flow path by the separate sleeve 21, the outer surface of the heat pipe itself could have a helical profile. In such an arrangement the entire heat exchanger would preferably be disposable. The flow path need not necessarily be helical but could have a zigzag, boustrophedon configuration.

At opposite ends 24 and 25, the inner sleeve 21 is sealed with an outer sleeve or housing 26, which is preferably of a thermally-insulative material such as a plastics material of low conductivity. The outer sleeve 26 is tubular with a smooth internal and external surface and extends coaxially as a close fit along the outside of the inner sleeve 21 so that the peak of the helical ridge 23 on the inner sleeve contacts the inner surface of the outer sleeve along its length. A short tubular spigot 27 projects outwardly at the right-hand end of the sleeve 26, adjacent the heater 17, and it is this that provides the inlet 3 of the heat exchanger 10. The spigot 27 opens into the sleeve 26 in alignment with the first valley between adjacent turns of the ridge 23 at the start of the helical flow path 20. At its opposite end, a similar spigot 28 opens into the valley at the final turn of the ridge 23, at the downstream end of the flow path 20 and provides the outlet 4 of the heat exchanger 10. The inner and outer sleeves 21 and 26 are sealed together at opposite ends 24 and 25 to prevent any escape of fluid and, together, form a flow path unit that can be slid off and removed from the heat pipe 12 and disposed of after use on one patient, or after a predetermined time. A new flow path unit can then be fitted on the heat pipe 12.

In use, the heat pipe 12 maintains a substantially equal and stable temperature along its length, which is communicated via its casing 13 to the inner sleeve 21 to warm the fluid flow path 20 along the outside of the heat pipe. Infusion fluid from the bag 1 flows along tubing 2 to the inlet 3 of the heat exchanger 10, typically at ambient temperature or at below ambient temperature if the bag has been refrigerated. As the fluid flows along the helical path 20 through the heat exchanger 10 it is gradually warmed until it emerges at the outlet 4 at a higher temperature, typically around the average body temperature of a human being of 37° C. It will be appreciated that, when the apparatus is used in veterinary applications, with animals having a different body temperatures, the temperature at the outlet may be set above or below 37° C. The warm fluid flows along tubing 5 to the catheter 6 and, from there, enters the patient's blood stream. The compact nature of the heat exchanger 10 means that it could be located close to the patient 7, thereby reducing the length of tubing 5 between the exchanger and the catheter 6 and consequently reducing ambient cooling of fluid flowing out of the exchanger.

If additional heating capacity is needed, such as in high flow applications or where the initial temperature of the infusion fluid is low, two or more heat exchangers could be connected in series one after the other.

The arrangement of the present invention can achieve a high thermal transfer to the infusion fluid in a relatively compact device and with minimal ambient cooling. It avoids the need for any re-circulating warming liquid as used in some prior fluid warmers. The apparatus can be very portable and could be battery powered, making it ideally suited for use in emergency situations away from the hospital. It is well recognised that a patient will have an increased chance of rapid recovery if infusion fluid is supplied at close to body temperature. Up to now this has been difficult to achieve away from a hospital. The heat pipe arrangement of the present invention gives a very stable temperature and reduces temperature fluctuations common in conventional electrical resistance heaters, which is of particular importance with fluids, such as blood, that can be damaged by excessive temperatures. The heat pipe does not require complex control circuits making the apparatus reliable and easy to use by relatively inexperienced clinicians. The apparatus requires few parts and can be made at relatively low cost.

The invention claimed is:

1. Medical infusion fluid heat exchange apparatus for warming medical infusion fluid, characterized in that the apparatus includes an elongate heat pipe of the kind containing a working fluid that operates using phase transition between a vapour and a liquid, a heat source mounted in thermal contact at one end of the heat pipe and an infusion fluid flow path extending along and around the outside of the heat pipe in thermal contact with the heat pipe, and that the heat source transfers heat to the heat pipe and the heat pipe transfers heat to the fluid flowing along the flow path, wherein the fluid flow path along the heat pipe has a length exceeding the length of the heat pipe.

2. Apparatus according to claim 1, characterized in that the fluid flow path extends helically along and around the outside of the heat pipe.

3. Apparatus according to claim 2, characterized in that the fluid flow path is provided between an inner sleeve of a thermally-conductive material having a helical external profile and an outer sleeve extending coaxially around the inner sleeve.

4. Apparatus according to claim 3, characterized in that a heat transfer substance fills space between the outside of the heat pipe and the inner surface of the inner sleeve.

5. Apparatus according to claim 3, characterized in that the outer sleeve is of a thermally-insulative material.

6. Medical infusion fluid heat exchange apparatus for warming medical infusion fluid, characterized in that the apparatus includes an elongate heat pipe of the kind containing a working fluid that operates using phase transition between a vapour and a liquid, a heat source mounted in thermal contact at one end of the heat pipe and an infusion fluid flow path extending along and around the outside of the heat pipe in thermal contact with the heat pipe, and that the heat source transfers heat to the heat pipe and the heat pipe transfers heat to the fluid flowing along the flow path, wherein the fluid flow path is separable from the heat pipe so that it can be removed and replaced for use on different patients.

7. Medical infusion fluid heat exchange apparatus for warming medical infusion fluid, characterized in that the apparatus includes an elongate heat pipe of the kind containing a working fluid that operates using phase transition between a vapour and a liquid, a heat source mounted in thermal contact at one end of the heat pipe and an infusion fluid flow path extending along and around the outside of the heat pipe in thermal contact with the heat pipe, and that the heat source transfers heat to the heat pipe and the heat pipe transfers heat to the fluid flowing along the flow path, wherein the heat source includes a positive temperature coefficient heater.

* * * * *